US010973408B2

(12) United States Patent
Lahiri et al.

(10) Patent No.: US 10,973,408 B2
(45) Date of Patent: Apr. 13, 2021

(54) SMART EYE SYSTEM FOR VISUOMOTOR DYSFUNCTION DIAGNOSIS AND ITS OPERANT CONDITIONING

(71) Applicant: Indian Institute of Technology Gandhinagar, Ahemedabad (IN)

(72) Inventors: Uttama Lahiri, Midnapur (IN); Anirban Dutta, Kolkata (IN); Abhijit Das, Kolkata (IN)

(73) Assignee: Indian Institute of Technology Gandhinagar, Ahemedabad (IN)

( * ) Notice: Subject to any disclaimer, the term of this patent is extended or adjusted under 35 U.S.C. 154(b) by 345 days.

(21) Appl. No.: 15/619,020

(22) Filed: Jun. 9, 2017

(65) Prior Publication Data

US 2017/0296048 A1 Oct. 19, 2017

Related U.S. Application Data

(63) Continuation of application No. PCT/IN2015/000448, filed on Dec. 11, 2015.

(30) Foreign Application Priority Data

Dec. 11, 2014 (IN) .......................... 3959/MUM/2014

(51) Int. Cl.
*A61B 3/113* (2006.01)
*A61B 5/00* (2006.01)
(Continued)

(52) U.S. Cl.
CPC ................ *A61B 3/113* (2013.01); *A61B 3/14* (2013.01); *A61B 5/0075* (2013.01);
(Continued)

(58) Field of Classification Search
CPC ......... A61B 3/113; A61B 3/14; A61B 5/0075; A61B 5/0205; A61B 5/04012;
(Continued)

(56) References Cited

U.S. PATENT DOCUMENTS 6,063,046 A 5/2000 Allum
2009/0018419 A1* 1/2009 Torch .................... A61B 3/112
600/318
(Continued)

FOREIGN PATENT DOCUMENTS

EP 2523724 11/2012
WO 2014164453 A1 10/2014

OTHER PUBLICATIONS

Anirban Dutta et al. (2013). Translational Methods for Non-Invasive Electrical Stimulation to Facilitate Gait Rehabilitation Following Stroke—The Future Directions. Neuroscience and Biomedical Engineering. 1. 22-33. 10.2174/2213385211301010005.*
(Continued)

*Primary Examiner* — Christopher Koharski
*Assistant Examiner* — James Moss
(74) *Attorney, Agent, or Firm* — Cowan, Liebowitz & Latman, P.C.; Mark Montague (57) ABSTRACT

Disclosed herein is a system that uses an eye tracker for diagnosing and facilitating rehabilitation therapy of a patient suffering from disability. The system creates a human machine interface (HMI) that integrates various low cost biosensors and artificial sensors for conducting rehabilitation therapy. The system combines spinal and supra-spinal feedback of the patient with the operant conditioning to facilitate visuomotor balance therapy (VBT), thereby reducing fall risk in disability survivors. The operant conditioning setup for shaping of visuomotor learning to bring about new behavior or to modify a certain aspect of an existing behavior is used for rehabilitation therapy that includes a behaviour response apparatus, a reward delivery module, a stimulus delivery system, and a behaviour control system. The system can also be extended to the patient's home for providing telerehabilitation therapy.

7 Claims, 2 Drawing Sheets

(51) Int. Cl.
*A61B 5/38* (2021.01)
*A61B 5/316* (2021.01)
*A61B 5/318* (2021.01)
*A61B 5/369* (2021.01)
*A61B 5/378* (2021.01)
*A61B 5/389* (2021.01)
*A61B 3/14* (2006.01)
*A61B 5/0205* (2006.01)
*A61B 5/11* (2006.01)
*A61B 8/10* (2006.01)
*A61B 5/0507* (2021.01)
*A61B 5/055* (2006.01)

(52) U.S. Cl.
CPC .......... *A61B 5/0205* (2013.01); *A61B 5/1103* (2013.01); *A61B 5/316* (2021.01); *A61B 5/318* (2021.01); *A61B 5/369* (2021.01); *A61B 5/378* (2021.01); *A61B 5/38* (2021.01); *A61B 5/389* (2021.01); *A61B 5/4023* (2013.01); *A61B 5/4064* (2013.01); *A61B 5/7278* (2013.01); *A61B 8/10* (2013.01); *A61B 5/055* (2013.01); *A61B 5/0507* (2013.01)

(58) Field of Classification Search
CPC .............. A61B 5/0402; A61B 5/04842; A61B 5/04845; A61B 5/0488; A61B 5/1103; A61B 5/4023; A61B 8/10; A61B 5/0507; A61B 5/055; A61B 5/0476; A61B 5/4064; A61B 5/7278
See application file for complete search history.

(56) References Cited

U.S. PATENT DOCUMENTS

| | | | | |
|---|---|---|---|---|
| 2009/0024049 | A1* | 1/2009 | Pradeep | G06Q 30/02 600/544 |
| 2012/0150545 | A1* | 6/2012 | Simon | A61B 5/0476 704/270 |
| 2014/0051044 | A1* | 2/2014 | Badower | A61B 5/165 434/236 |
| 2014/0330159 | A1 | 11/2014 | Costa et al. | |
| 2016/0235323 | A1* | 8/2016 | Tadi | A61B 5/7285 |
| 2017/0231490 | A1* | 8/2017 | Toth | A61B 5/40 600/558 |

OTHER PUBLICATIONS

Hong Zeng et al., "Removal of EOG Artifacts from EEG Recordings Using Stationary Subspace Analysis," The Scientific World Journal, vol. 2014, Article ID 259121, 9 pages, 2014. https://doi.org/10.1155/2014/259121.*

Yunyong Punsawad et al., "Hybrid EEG-EOG brain-computer interface system for practical machine control". Conf Proc IEEE Eng Med Biol Soc. 2010;2010:1360-3. doi: 10.1109/IEMBS.2010.5626745. https://ieeexplore.ieee.org/document/5626745. viewed on Oct. 7, 2019.*

W. Zheng, B. Dong and B. Lu, "Multimodal emotion recognition using EEG and eye tracking data," 2014 36th Annual International Conference of the IEEE Engineering in Medicine and Biology Society, Chicago, IL, 2014, pp. 5040-5043. doi: 10.1109/EMBC.2014.6944757.*

Arindam Dutta et al. "A Low-Cost Point-of-Care Testing System for Psychomotor Symptoms of Depression Affecting Standing Balance: A Preliminary Study in India," Depression Research and Treatment, vol. 2013, Article ID 640861, 8 pages, 2013. https://doi.org/10.1155/2013/640861. viewed on Oct. 7, 2019.*

A. Dutta, A. Banerjee and A. Dutta, "Low-cost visual postural feedback with Wii balance board and Microsoft Kinect—a feasibility study," 2013 IEEE Point-of-Care Healthcare Technologies (PHT), Bangalore, 2013, pp. 291-294. doi: 10.1109/PHT.2013.6461342.*

Dutta A, Lahiri U, Das A, Nitsche MA and Guiraud D(2014), Post-stroke balance rehabilitation under multi-level electrotherapy: a conceptual review. Front. Neurosci. 8:403. doi:10.3389/fnins.2014.0040.*

* cited by examiner

SMART EYE SYSTEM FOR VISUOMOTOR DYSFUNCTION DIAGNOSIS AND ITS OPERANT CONDITIONING

FIELD OF THE INVENTION

The present invention relates to a portable apparatus for measuring eye movement of subjects, methods for diagnosing and treating neurological and psychiatric disorders using such an apparatus, and for providing therapeutic central and peripheral neurostimulation based upon the detected eye movement abnormalities. More particularly, the present invention relates to a system that provides eye movement based quantitative, non-invasive diagnosis, and shaping of visuomotor learning to bring about new behavior or to modify a certain aspect of an existing behavior using neurostimulation for rehabilitation of various neurological and psychiatric disorders where eye-movement abnormalities are common.

BACKGROUND OF THE INVENTION

In normal day-to-day functioning, human beings need to have accurate and precise eye movements to various sensory stimuli. The complex neural pathways and brain regions involved in production of eye movements during ocular fixation and gaze control include a widely distributed network in the area of brain that includes the cerebrum, brainstem, and cerebellum. The widely distributed network is affected by various neurological and psychiatric disorders in a typical manner, producing characteristic eye movement gaze abnormalities. These eye movement gaze abnormalities provide a diagnostic clue to the underlying condition or disease of the subject. Thus, quantitative recordings of eye movements provide valuable information about the severity, progression or regression of the underlying condition or disease. Further, the quantitative readings provide an objective to evaluate the efficacy of neuro-protective and neuro-restorative therapies. For example, aspects of saccades, i.e., a type of rapid continuous eye movement, can be tested to probe both motor and cognitive aspects of oculomotor behavior.

Saccades help to re-fixate the eye from one object to another. Fixations are separated by saccades to constitute a scan path and are defined as movements of the eye from one point to another. Smooth pursuits can be described as fixation-in-motion and they occur when the eyes are following a moving target. Any deviation from the normal conditions of the aforementioned parameters results in abnormalities such as nystagmus, saccadic palsy and strabismus.

Nystagmus is a condition that causes involuntary rapid movement of one or both the eyes. The eyes may move from side to side, up and down or in a circular motion. Saccadic palsy involves loss of voluntary movement on the contralateral side and is due to cortical damage or a lesion of the paramedian pontine reticular formation in the brainstem pons. The damage to the motor neurons of ocular muscles results in paralysis of the muscle that is often manifested as a Strabismus. The external manifestation of various Parkinsonian disorders and stroke can cause irregularities in blinking. The rate of blinking of the eyes reduces due to incomplete and irregular eye closure.

Different types of oculomotor deficits, as mentioned above, can be used as sensitive bio-markers for various neurological and psychiatric disorders. Many systems and devices are known in the art to tackle problems related to oculomotor deficits. A three-step bedside oculomotor examination system—HINTS acronym for Head-Impulse-Nystagmus-Test-of-Skew can diagnose disabilities in a period of 24-48 hours and is better than a negative MRI with diffusion weighted imaging (DWI). However, expertise in these bedside techniques is limited to specialists. Hence, there is a need for a home-based monitoring and telerehabilitation system, which is not only as accurate as HINTS, but also easy to use.

In a particular rehabilitation application, subjects suffering from stroke are at a high risk for falls. When a person's balance is disturbed, his or her postural stability is maintained with the help of feedback mechanisms received from the brain. In existing feedback mechanisms, operant conditioning for rehabilitation of subjects has been used in isolation. A low-cost posturography system that quantifies postural control when the body is in the upright position has been developed to study center of pressure-center of mass (CoP-CoM) trajectories during voluntary weight-shifting tasks assigned to the subjects. Electromyography (EMG) signals of the subjects were collected and it was observed that muscle responses in a paretic limb were delayed as compared to muscle responses in a sound limb. This research also suggested that agility training programs that challenge dynamic balance may be more effective than static stretching or weight-shifting exercise programs in preventing falls during treatment of the subjects. It also leads to the conclusion that spinal and supra-spinal multisensory integration, in addition to muscle strength, is critical for balance recovery.

Another technique for rehabilitation of the subjects called functional electrical stimulation (FES) that includes neuromuscular electrical stimulation (NMES) of motor nerves and muscles as well as sensory electrical stimulation (SES) of the sensory nerve has been developed to facilitate post stroke therapy. NMES involves a device that sends a series of electrical signals to a group of muscles through electrodes, causing stimulation of the muscles. Prior research shows that NMES evokes lasting changes in corticospinal excitability, where volitionally driven NMES with real time visual feedback may induce neuroplasticity in spinal circuits.

Indeed, feedback mechanisms controlled by the cerebral cortex play an important role during postural perturbations. Further, another research concludes that non-invasive brain stimulation, especially transcranial direct current stimulation (tDCS) facilitates rehabilitation of subjects by modulating cortical excitability at cerebral cortex. Modulation of cortical excitability is achieved by passing a weak current directly to the brain, thereby enhancing sensory feedback and motor control that facilitates the neuroplasticity mechanism. For an example, anodal tDCS over sensorimotor cortex leads to an increase in the size of the ipsilateral cortical component of the somatosensory system and therefore enhances corticospinal excitability. Further, anodal tDCS over primary motor cortex increases di-synaptic inhibition by increasing di-synaptic interneuron excitability and thereby affects spinal network excitability as well.

Significant research has been done in the past in the area of rehabilitation for subjects by using neuro-stimulation techniques that can be interfaced with a portable apparatus for measuring eye movement for visuomotor rehabilitation. However, none of these pioneering research works in the area of rehabilitation for visuomotor disabilities has used a closed-loop integrated approach where operant conditioning is performed to bring about new behavior or to modify a certain aspect of an existing behavior towards rehabilitation of the visuomotor deficits.

Further, US 2014/0330159 discloses a system for assessing a patient's neurological disability by the means of neuromotor or visuomotor task and recording the patient's performance depending on a level complexity of the task. WO 2014/164453 discloses a method to assess a subject's neurological and psychological status using visual tests. The visual tests include signals from a responsive eye movement, a non-responsive eye movement, an involuntary eye movement, a responsive body movement, a non-responsive body movement, and an involuntary body movement. The accuracy of the movements determines the subject's neurological and psychological status depending upon the performance validity. Although both the patents disclose diagnosis of neurological and psychological disabilities of a patient, they do not disclose any information on integrating the visual feedback with the body movements in order to treat the patient diagnosed with the neurological and psychological disabilities.

In an embodiment presented here for post-stroke balance rehabilitation, the primary focus is on improving the standing balance ability of the stroke patient. In light of the foregoing discussion, we present an embodiment of the system that can apply an eye gaze based diagnostics during a visuomotor task to identify the deficits. Furthermore, we present an embodiment for a system that provides a real time adaptive visual feedback as well as electrical stimulation (NMES and SES) to shape visuomotor learning facilitating normal behaviour while penalizing compensatory mechanisms thereby leading to an effective visuomotor balance rehabilitation therapy for survivors from disabilities.

Objects

An object of the present invention is to provide a low-cost eye tracker based system to be used as a diagnosis tool for patients suffering from visuomotor dysfunction.

Another object of the present invention is to leverage the low-cost eye tracker based system to identify visuomotor dysfunction and guide neuromuscular electrical stimulation (NMES) and sensory electrical stimulation (SES) based visuomotor rehabilitation therapy for patients by combining spinal and supra-spinal feedback. Here, the object of the present invention is to provide an eye tracking-based sensorimotor operant conditioning with the NMES and the SES for visuomotor disability in the patients.

Yet another object of the present invention is to provide an eye tracking based sensorimotor operant conditioning for tele-rehabilitation therapy that can be extended to a patient's residence, where a care-taker can remotely monitor the progress of his or her health and identify improvement areas.

SUMMARY

According to an embodiment of the invention, a system includes an eye tracker for measuring various eye parameters to diagnose the patient during a visuomotor and/or oculomotor task, the system also includes biosensor units that measure bio-signals, motion sensors, first and second Bayesian sensor fusion modules, an electrical stimulator, a signal generator, a near normal kinematic module, and a processor. In conjunction with all the elements, the system is configured to enforce muscle activity using the NMES and sensory activity with the SES, enhance muscle activity task specific beneficial learning using operant conditioning, and stimulate the neural circuits of the brain using non-invasive brain stimulation (NIBS).

The first objective i.e., enforcement of normative muscle movement is achieved by providing the NMES and SES in the form of electrical signals to the neuromuscular system. The electrical stimulation is provided by the electrical stimulator. The evoked muscle activity generates a volitional EMG signal, which is detected by a biosensor unit such as an EMG device. The motion sensors detect the positioning and movement of the patient. The volitional EMG signal and the signal detected by the motion sensors are fed to the first Bayesian sensor fusion module. Based on the first Bayesian sensor fusion module, muscle and sensory nerve activation templates are produced by the signal generator. The signal generator transfers the generated templates to the electrical stimulator. The muscle activation and sensory activation templates trigger the electrical stimulator to provide stimulation to the spinal system.

During a visuomotor task, the eye tracker detects abnormalities in the eye movements of the patient and provides an eye gaze data to the second Bayesian sensor fusion module. The eye movement results in stimulation of cortical neurons, which is detected by a biosensor such as an electroencephalography (EEG) device. The EEG device generates an EEG data. The EEG data is provided to the second Bayesian sensor fusion module. Based on the second Bayesian sensor fusion module, brain nerve activation templates are produced by the signal generator. The brain nerve activation templates are provided to the brain for corrective cortical action. Under the visuomotor task, the brain sends an improved motor control signal to the spinal system and enhances the muscle activity of the patient, thereby achieving therapeutic effect.

The third objective is to trigger and stimulate the neural circuits of the brain related to the visuomotor task with neurostimulation, in conjunction with volitionally driven FES (NMES and SES) stimulator. The NMES and SES received from the electrical stimulator and NIBS facilitated motor control signal received from the brain lead to the enhanced excitation and contraction of the musculo-skeletal system, which is controlled by the spinal system. Evoked torque and volitional torque generated from the muscles are superimposed and fed to the near normal kinematic module. The output of the near normal kinematic module generates a near normal afferent feedback signal, which is provided to the brain for sensorimotor integration. Thus, the pathological areas of the brain are stimulated non-invasively by using the neurostimulation technique at the central nervous system level in conjunction with FES (NMES and SES) at the peripheral nervous system level. This setup is amenable to tele-neurorehabilitation.

According to another embodiment of the invention, the system includes a portable apparatus for measuring eye movements to diagnose patients suffering from visuomotor disability, and facilitate visuomotor balance therapy (VBT) under an operant conditioning paradigm. The VBT is used to reduce risk of falling in patients by the integration of spinal and supra-spinal feedback, thereby enhancing the limb-eye coordination of patients.

According to an embodiment of the invention, a method for diagnosing visuomotor dysfunction of a subject during a visuomotor task includes the following steps:
  monitoring eye parameters of the subject;
  detecting a bio-signal of the subject;
  sensing physical parameters of the subject, and
  diagnosing a visuomotor dysfunction based on the eye parameters, the bio-signal, and the physical parameters of the subject.

According to another embodiment of the invention, a method for closed loop stimulation of central nervous system (CNS) in conjunction with peripheral nervous system (PNS) of a subject in a treatment of visuomotor dysfunction includes the following steps:

monitoring eye parameters of the subject and generating an eye gaze data based on the eye parameters;

detecting cortical biosignal data and spinal biosignal data of the subject;

sensing physical parameters of the subject;

generating a first output signal based on the cortical biosignal data and the eye gaze data;

generating a second output signal based on the spinal biosignal data and physical parameters;

generating a plurality of stimuli based on the first and second output signals; and stimulating the central nervous system (CNS) and the peripheral nervous system (PNS) of the subject based on the plurality of stimuli.

According to yet another embodiment of the invention, a method for operant conditioning with a subject in loop during a visuomotor task in a treatment of visuomotor dysfunction includes the following steps:

monitoring eye parameters of the subject and generating an eye gaze data based on the eye parameters;

detecting cortical biosignal data and spinal biosignal data of the subject;

sensing physical parameters of the subject;

generating a first output signal based on the cortical biosignal data and the eye gaze data;

generating a second output signal based on the spinal biosignal data and physical parameters;

generating a plurality of stimuli based on the first and second output signals;

delivering a spatiotemporally patterned stimulus coordinated with a visuomotor behavior to central nervous system (CNS) and peripheral nervous system (PNS) of the subject by a way of the plurality of stimuli for shaping of visuomotor learning by a way of perceptual and attentional learning approaches; and delivering a spatiotemporally patterned reward coordinated with the visuomotor behavior to the subject by a way of the plurality of stimuli for shaping of the visuomotor learning, thereby prodding the subject to use affected portion more than unaffected portion to perform the visuomotor task and reducing compensatory mechanisms of the unaffected portion of the subject.

BRIEF DESCRIPTION OF DRAWINGS

The features of the present invention, which are believed to be novel, are set forth with particularity in the appended claims. Embodiments of the present invention will hereinafter be described in conjunction with the appended drawings provided to illustrate and not to limit the scope of the claims, wherein like designations denote like elements, and in which:

DETAILED DESCRIPTION OF EMBODIMENTS

As used in the specification and claims, the singular forms "a", "an" and "the" include plural references unless the context clearly dictates otherwise. For example, the term "an article" may include a plurality of articles unless the context clearly dictates otherwise.

Those with ordinary skill in the art will appreciate that the elements in the Figures are illustrated for simplicity and clarity and are not necessarily drawn to scale. For example, the dimensions of some of the elements in the Figures may be exaggerated, relative to other elements, in order to improve the understanding of the present invention.

There may be additional components described in the foregoing application that are not depicted on one of the described drawings. In the event such a component is described, but not depicted in a drawing, the absence of such a drawing should not be considered as an omission of such design from the specification.

Before describing the present invention in detail, it should be observed that the present invention utilizes a combination of system components which constitutes an eye tracking system that helps in diagnosis as well as helps in visuomotor rehabilitation of patients suffering from visuomotor dysfunction. Accordingly, the components and the method steps have been represented, showing only specific details that are pertinent for an understanding of the present invention so as not to obscure the disclosure with details that will be readily apparent to those with ordinary skill in the art having the benefit of the description herein.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting but rather to provide an understandable description of the invention.

As used herein, the term "subject", "person", "survivors" or "patient" refers to any human, including a healthy human, a human diagnosed with or at risk of a neurological and/or psychological condition, a human being monitored for or undergoing treatment for a neurological and/or psychological condition, or a human whose neurological and/or psychological status is being assessed or monitored for any reason. These terms are interchangeably used in the present disclosure.

Various embodiments of the invention described herein focus primarily on diagnosis and treatment of a patient suffering from a visuomotor disability by using an eye tracker along with central and peripheral electrical stimulation under an operant conditioning paradigm. These embodiments provide a system that stimulates the central nervous system through a combination of rehabilitation therapies that facilitates neural circuits of the brain to provide a therapeutic benefit. Various embodiments of the present invention are integrated with each other in the low-resource environment forming tele-neurorehabilitation system.

Figure 1:
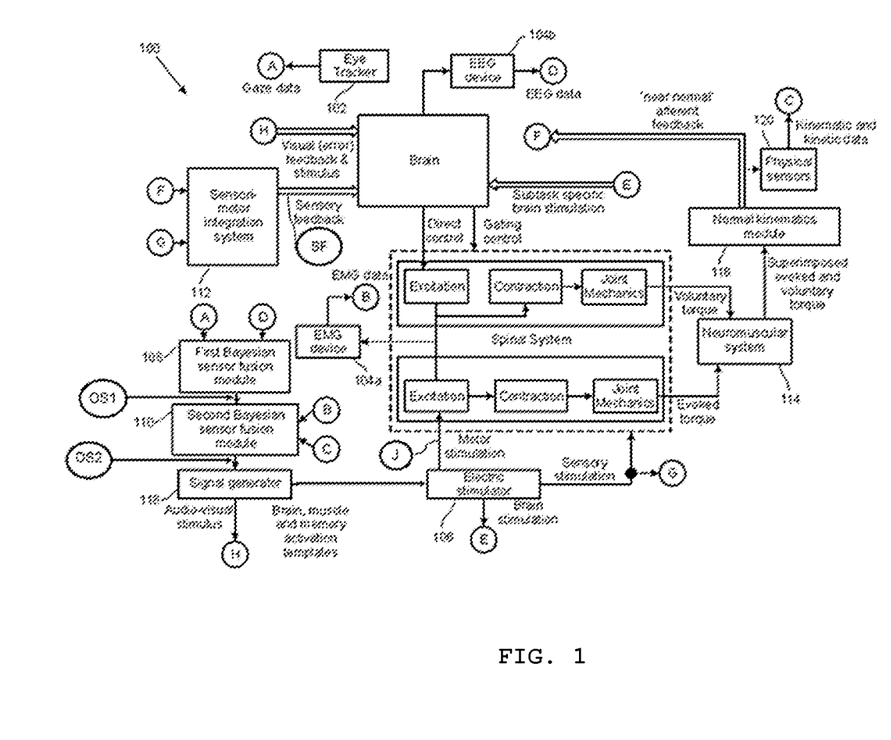
FIG. 1 shows a representative block diagram of a system used for facilitating rehabilitation therapy for subjects using sensory motor operant conditioning, according to an embodiment to the present invention.

A system 100 for diagnosing and treating a patient suffering from the visuomotor disability is shown in FIG. 1. The system 100 is configured to provide an eye gaze-based pre-screening diagnosis tool to the patient. Further, the system 100 is configured to provide therapeutic stimulation, facilitate sensorimotor operant conditioning and apply neurostimulation to the patient suffering from the visuomotor disability. In one embodiment, the visuomotor disability is due to at least one of stroke, brain injury, heart ailment, neurological disorder, eye condition, muscle malfunction, psychosomatic disorder, psychomotor disorder, and physical disorder.

Generally, the gravity and the form of disability due to a stroke, Parkinsonisms or traumatic brain injury may vary in patients. The system 100 detects the visuomotor disability specific to the patient under observation by recording various eye and body movement parameters, and implements a visuomotor rehabilitation therapy. In other words, the system 100 is not only used as a tool to diagnose a patient suffering from the visuomotor disability, but also serves as a device for treating the visuomotor disability. An operant conditioning setup for the patient suffering from the visuomotor disability includes a behaviour response apparatus, a reward delivery module, a sensory stimulus delivery system, and a behaviour control system. The behaviour response apparatus is a low-cost human machine interface that computes the kinetics and kinematics of the body during visuomotor balance therapy (VBT). The reward delivery module is a visual feedback system that comprises a cursor controller, which maps body movements to cursor trajectories that are projected to the patient in a virtual environment during the VBT. The cursor controller makes the VBT easier for the affected side of the body and difficult for the unaffected side of the body such that the patient uses the affected side more often for the VBT. The sensory stimulus delivery system includes a functional electrical stimulation (FES) system and a visual stimulus delivery system. In an embodiment, the FES system generates at least one of a neuromuscular electrical stimulation (NMES) and a sensory electrical stimulation (SES). Further, the visual stimulus delivery system is used to provide visual cues for the VBT. The behaviour control system uses the NMES system for muscle stimulation (J) to constrain compensatory mechanisms and enforces normative movements of the body under an operant conditioning paradigm. In an embodiment, the reward delivery module, for the visuomotor task, delivers rewards by various means including modulating the scores, varying the difficulty, and/or providing pleasant sensory events to the subject.

The operant conditioning paradigm leverages perceptual and attentional learning, wherein task-irrelevant perceptual learning (TIPL) stimuli, such as stimuli due to maladaptive plasticity post-stroke, may be enforced during task-performance. Here, an eye tracking system is leveraged to measure the engagement of the patient suffering from visuomotor disability with the task-performance to further enforce a task-relevant engagement. The task-relevant engagement is attained using sensory stimulus (G) to facilitate attentional learning that may suppress task-irrelevant stimuli to constrain compensatory mechanisms. The scientific basis of the operant conditioning paradigm is to monitor the learning process using at least one of attentional, reinforcement, and reward gating systems that are used to shape the behaviour during rehabilitation. The rehabilitation is facilitated by beneficial learning while suppressing compensatory mechanisms. Further, affected part of the visuomotor system is exposed repetitively to the task than the unaffected part in order to improve task performance. Furthermore, neurostimulation is used as a behaviour modulator by facilitating a normative brain function and inhibiting the brain dysfunction. In an embodiment, the brain acts as a controller for the VBT to drive the visuomotor task via the presented human machine interface. In another embodiment, the brain is modulated by the central and peripheral stimulation to facilitate the visuomotor task performance by the patient suffering from the visuomotor disability.

The system 100 comprises an eye gaze tracker module 102 to diagnose abnormalities in the eye movements of the patient, according to various embodiments of the invention. In an embodiment, the eye gaze tracker module 102 comprises a desktop remote device with an inbuilt camera, an infrared emitter, frame grabbers, an optical filter and a controller with an algorithm for processing an image obtained through a video oculography. All the components work in conjunction to track the eye movements of the patient. Further, the eye gaze tracker module 102 measures various other eye parameters such as saccades, fixation pattern, smooth pursuit behaviour, and the like, to diagnose various disabilities or disorders of the patient. The measured pattern of the eye movements is used for quantitative analysis of the condition or disease of the patient. An eye gaze data (A) is acquired based on the eye parameters. It should be appreciated, hereinafter, that the terms eye gaze tracker module 102 and eye tracker 102 are used interchangeably.

The system 100 for diagnosing a patient suffering from the visuomotor disability includes the eye gaze tracker 102, biosensor, and physical sensor 120. The biosensor detects a bio-signal measured from the body due to the patient's muscle activity. In an embodiment, the bio-signal may be at least one of electromyogram (EMG) signal and an electro-encephalography (EEG) signal. The physical sensor 120 detects physical parameters on the basis of positioning and movement of the body. In an embodiment, the physical parameters are at least one of centre of pressure (CoP) and centre of mass (CoM). The eye parameters, bio-signal, and physical parameters are analysed for diagnosing the patient suffering from the visuomotor disability.

According to an embodiment of the invention, the system 100 is configured to achieve three objectives to provide the rehabilitation therapy to the patient. The system 100 creates a human machine interface (HMI) to facilitate diagnostics and the rehabilitation therapy as shown in FIG. 1. The HMI is a web based interface for connecting, configuring and controlling the system 100. The system 100 makes use of the HMI to assist interaction between the brain and various parts of the patient's body. In this embodiment, the three objectives attained by the system 100 during the rehabilitation therapy include—enforcing a normative muscle activity using the therapeutic NMES, promoting a normative residual muscle activity using the operant conditioning, and facilitating the normative neural circuits of the brain using various neurostimulation methods.

The system 100 described in the present invention, in whole or in part, can be implemented on a computer system or network. For the purpose of this disclosure, modules such as first and second Bayesian sensor fusion modules 108 and 110 and signal generator 118 are a part of the computer system. A suitable computer system includes at least, a processor and memory; optionally, a computer-readable medium that stores computer code for execution by the processor. Once the code is executed, the computer system carries out the described methodology.

In this regard, a "processor" is an electronic circuit that can execute computer programs. Suitable processors are exemplified by but are not limited to central processing units, microprocessors, graphic processing units, digital signal processors, network processors, front end processors, coprocessors, data processors and audio processors. The term "memory" connotes an electrical device that stores data for retrieval. In some embodiments, therefore, a suitable memory is a computer unit that preserves data and assists computation. More generally, suitable methods and devices for providing the requisite network data transmission are known. Also contemplated is a non-transitory computer readable medium that includes executable code for carrying out the described methodology. In certain embodiments, the medium further contains data or databases needed for such methodology.

A representative block diagram of the system 100 performing the rehabilitation therapy is shown in FIG. 1. In addition to the eye gaze tracker 102, the system 100 comprises spinal biosensor such as an electromyogram (EMG) device 104a, cortical biosensor unit such as an electroencephalography (EEG) device 104b, an electrical stimulator 106, a first (cognitive) Bayesian sensor fusion module 108, a second (spinal) Bayesian sensor fusion module 110, a sensorimotor integration system 112, a neuromuscular system 114, a near normal kinematics module 116, a signal generator 118 and the physical sensors 120. The physical sensor 120 includes at least one of motion sensors such as passive infrared (PIR) sensors, inertial measurement unit, 3D camera, depth sensor, microwave sensors, ultrasonic motion, and vibration motion sensors or combinations thereof. It should be appreciated that the use of any other motion sensor is well within the scope of the present invention. In an embodiment, each of the cortical and spinal biosensors is at least one of an electroencephalography (EEG) device, EMG device, an electrocardiography (ECG) device, an electrodermography (EDG) device, a diffuse optical imaging system, and a magnetic resonance imaging device (MRI). All the aforementioned elements work in conjunction with each other to achieve the three objectives of the system 100.

The first objective of the system 100 is to achieve the therapeutic electrical stimulation, i.e., the electrical stimulation of the sensory and motor nerves, and muscles as shown in FIG. 1. The eye gaze tracker 102 receives eye parameters based on the patient's eye movement with respect to a certain task and sends a visual feedback to the patient's brain. The brain controls the patient's spinal system, which in turn controls the patient's musculoskeletal system. The spinal system is controlled by the brain by at least one of a direct control and a gating control. In case of the direct control, muscles are directly controlled by the brain via alpha motor neuron to perform certain motor tasks. However, in case of the gating control the brain modulates the spinal reflexes to perform certain "automatic" motor tasks.

Further, the spinal system receives the sensorimotor stimulation from the electrical stimulator 106 in the form of electrical signals. Based on the visual feedback signal received from the brain and the stimulation received from the electrical stimulator 106, the spinal system actuates muscle cells. The stimulation of the spinal system results in the excitation and contraction of muscles which in turn causes the movement of various body parts along with the joints. To achieve the first objective, at least two signals are monitored. The two signals include a first signal and a second signal. The first signal is a bio-signal measured from the body due to the patient's muscle activity. In an embodiment, the bio-signal may be at least one of EMG, EEG, ECG, EDG, and MRI. In one example, the muscle activity is in the form of an EMG signal. In another example, the muscle activity is in the form of an EEG signal. The EMG device 104a detects the EMG signal and the EEG device 104b detects the EEG signal. The EEG signal is a cortical biosignal and EMG signal is a spinal biosignal. Both EMG signal and EEG signal are generated due to the muscle activity evoked by stimulation as well as voluntarily. The EMG signal and EEG signal results in formation of EMG data (B) and EEG data (D). The physical sensor 120 detects the second signal in the external world on the basis of a positioning and movement of the body. In an embodiment, the position and movement of the body are sensed by the way of physical parameters such as centre of pressure (CoP) and centre of mass (CoM) signals (C).

Further, the eye gaze data (A) of the eye gaze tracker 102, bio-signals, which include EEG signals, are given as a first input and a second input, respectively to the first (cognitive) Bayesian sensor fusion module 108 to generate a first output signal (OS1) which is a signal received from the central nervous system of the subject. The bio-signals which include the EMG data (B) and the physical parameters (C) are provided as first and second inputs, respectively to the second (spinal) Bayesian sensor fusion module 110. The second Bayesian sensor fusion module 110 generates a second output signal (OS2) which has the component of the first output signal (OS1), and the second output signal (OS2) is also generated based on the spinal biosignal data and physical parameters. Based on first and second Bayesian sensor fusion modules 108 and 110, the audio-visual stimulus and brain, muscle, and sensory nerve activation templates (also referred as stimuli) are produced by the signal generator 118 that are transferred to the electrical stimulator 106. The electrical stimulator 106 generates an output signal to stimulate central nervous system (CNS) in conjunction with peripheral nervous system (PNS).

For example, if the patient desires to move his arm from one position to another, the eyes set the target and send a visual feedback stimulus (H) to the brain. Based on the visual feedback stimulus (H), the brain inturn provides a motor command to the spinal system commanding it to actuate the muscles of the arm to perform the desired action. If the muscles are unable to receive stimuli by the spinal system, the signal generator 118 will send a signal to the electrical (NMES) stimulator 106 in the form of muscle activation templates. The electrical (NMES) stimulator 106 provides a therapeutic electrical stimulation (J) to the muscles, thereby assisting the movement.

The second objective is to conduct the operant conditioning by modulating sensorimotor integration (112) to improve the residual normative function. The operant conditioning paradigm incorporates the bio-feedback mechanism to aid the patient's disability. The operant conditioning aims at reducing the error of the muscle and the eye movement, by sending two types of signals to the brain i.e., a visual error feedback stimulus (H) using the signal generator 118 and a near-normal sensory feedback (SF) using the sensorimotor integration system 112.

The visual error feedback stimulus (H) is a visual stimulus of the error between the patient's volitional movement trajectory and a normative trajectory during the visuomotor rehabilitation therapy. The normative trajectory is the generated from a healthy individual's body movement. In an embodiment, the normative trajectory is age-matched.

In another embodiment, the visual error feedback stimulus (H) may be accompanied with an audio signal given by a speaker (not shown) connected to the signal generator 118 and its frequency and/or pitch can be modulated based on the error between the patient's volitional movement trajectory and the normative trajectory. The near normal sensory feedback stimulus (H) is provided to the brain by electrical stimulation of the sensory nerves (SES) using the electrical stimulator 106.

In one embodiment, the visual error feedback stimulus (H) provided to the brain is a task specific. For example, if the patient tries to move his hand from position A to position B, but is able to do so only using abnormal compensatory muscle activations, then the patient will try to reduce that error using the visual error feedback stimulus (H) given to the brain. The task specific visual error feedback stimulus (H) from signal generator 118 is with respect to a normative muscle activation captured with a normative EMG data (B). In one embodiment, the normative EMG data is captured from a healthy age-matched individual performing the same task. A normative EMG data is generated by the second Bayesian sensor fusion module 110 that performs inverse kinematics by using probabilistic modelling techniques based on the cognitive prior from the first Bayesian sensor fusion module 108. Bayesian motion control and planning is based on the fusion of several normative motion objectives, such as constraints, goals, priors, and the like using probabilistic inference techniques.

Further, the volitional EMG data (B) and the normative EMG data are sent by the second Bayesian sensor fusion module 110 to the signal generator 118. The signal generator 118 compares the volitional EMG signal and the normative EMG signal, and if the volitional EMG signal deviates from the normative EMG signal, the signal generator 118 generates a first visual error feedback stimulus (H). The eye gaze tracker 102 detects deviation in the patient's engagement to the task as evident from the eye parameters and sends an engagement based feedback signal to the first Bayesian sensor fusion module 108 that sends the cognitive aspect, i.e. engagement, to the signal generator 118, which compares with normative data and generates an eye-limb co-ordination error signal. The eye-limb co-ordination error signal is provided to the brain. In one embodiment, the patient may lack engagement with the task that is too difficult or too easy, therefore depending on the engagement based feedback signal the signal generator 118 changes the task difficulty level (e.g. VBT) during rehabilitation therapy.

Similarly, the evoked muscle activity is super-imposed with the volitional muscle activity in the neuromuscular system 114 and passed through the near normal kinematics module 116 to generate a 'near normal' afferent feedback (F) which is sent to the brain. Also, the signal generator 118 generates the sensory feedback signal using electrical (SES) stimulator 106 and sends the sensory feedback signal (SF) to the sensorimotor integration system 112. The sensorimotor integration system 112 integrates near normal afferent feedback signal (F) and sensory feedback signal (SF) to generate a near normal sensory feedback signal which is sent to the brain. Based on visual error feedback stimulus (H) and the near normal sensory feedback signal (SF), the brain sends a motor control signal to the spinal system.

For example, if one eye has an impaired vision, the vision of the impaired eye is enhanced by providing a differential visual stimulus to the eyes such that the vision is facilitated in the impaired eye. Here, in one embodiment, the luminance contrast of the dots (100% coherence) can be adapted for the presentation of the visual stimulus such that it is lower for unaffected eye that is possibly inhibiting the affected eye. This whole process is referred as the operant conditioning using sensory stimulus (G) such that the brain perceives the ability of the affected part at par with the unaffected part.

In the operant conditioning, the system 100 reduces the error committed by the patient while performing a desired task by the means of the visual error feedback stimulus (H) and the near-normal sensory feedback signal (SF) to the brain. In this case, the signal generator 118 sends the visual error feedback stimulus (H) and the near-normal sensory feedback signal (SF) to the brain as discussed above. In an embodiment, the near normal sensory feedback signal (SF) to the brain is modulated artificially using at least one of the electrical stimulation and the visual stimulation such that the brain perceives the affected side equivalent to the unaffected side for sensorimotor integration. Therefore, when the brain acts as a controller for the visuomotor task and sends a control signal to the spinal system that is evaluated in terms of the error with respect to the normative signal, the brain considers the affected parts at par with the unaffected parts for the visuomotor task performance. If there is still a volitional error then the error feedback is provided to the patient so that the patient may volitionally try to reduce the error. Further, the spinal system upon receiving the modified control signal enhances the muscle activity thereby improving the action. In one embodiment, the neurostimulation methods may facilitate learning such that the error converges faster to zero.

The third objective of the system 100 is to stimulate neural circuits with the CNS neurostimulation methods in conjunction with the electrical stimulator 106. The spinal system controls the musculoskeletal system of the human body. The musculoskeletal system can be controlled voluntarily by the brain or by the electrical stimulator 106. The stimulation of spinal system by the electrical stimulator 106 results in generation of an evoked torque, while the stimulation of spinal system by the brain results in generation of a voluntary torque.

For an example, in the present embodiment, the brain stimulation (E) is generated for a subtask.

The brain stimulation signal (E) is given to the brain for modulating the brain cells. The brain upon receiving modulation sends a better motor control signal to the spinal system. Thus, the NIBS technique is used to modulate the brain cells to volitionally send a better motor control signal to the spinal system whenever an incorrect action is performed by the patient.

The subtask specific brain stimulation signal is targeted to cortical neuronal sources based on advanced signal processing techniques, such as dynamic imaging of coherent sources (DICS) performed by the first (cognitive) Bayesian sensor fusion module 108 for the cortical sources that act as prior for the second (spinal) Bayesian sensor fusion module 110 for cortico-muscular sources. These signal processing techniques are well suited to identify the transient cortical networks involved in movement in heterogeneous brain disability. The cortical networks are identified on the basis of a signal obtained by mobile brain body imaging (MOBI) methods, which allows the EEG and the EMG recordings during the movement. In an embodiment, the EEG and the EMG signals are combined and recorded online and further subjected to coherence analysis. The anatomical location of the brain which needs to be stimulated is identified by using a magnetic resonance imaging (MRI). A high-resolution, T1-weighted MRI covering the entire skull is obtained for each patient. In this MRI, five tissue types are distinguished, namely, white matter (WM), gray matter (GM), cerebrospinal fluid (CSF, including the lateral ventricles), skull, and skin, in addition to manual segmentation of post-disability lesions. Cerebellum and brain stem is treated as WM, and the GM volume is divided into a regular grid to calculate the lead-potential at each grid point, that is computed assuming isotropic tissue conductivity using boundary element method (BEM). If anisotropic conductivity for WM and GM, i.e., derived from diffusion tensor imaging (DTI) signal is needed for better accuracy of the cortical source location from the EEG signal, finite element method (FEM) is applied. A beam former using DICS is applied on the EEG and the EMG signals, where DICS uses correlations in the frequency domain (a cross-spectrum density matrix) for source estimation using the lead-field for optimizing the inverse solution. In an embodiment, two measures, a first measure and a second measure, are derived from the cross spectral matrix. The first measure is a power spectrum of the signals represented by the diagonal element, which allows identification of frequency bands containing most of the power or those showing sub-task dependent changes. The second measure is a coherence (bounded between 0 and 1), which is the magnitude-squared cross spectrum in the off-diagonal elements divided by the power spectra of both time series. The coherence is used for estimating functional connectivity between the brain areas (corticocortical) and also peripheral muscles (corticomuscular). Further, the coherence is applied for characterization of cortical networks involved in healthy movements that allows investigation of corresponding pathological connectivity in post-disability patients. Specifically, corticomuscular (EEG-EMG) coupling with peripheral EMG signals for the muscle module of a movement subtask is identified first, and then the cortical area showing the strongest coherence with peripheral EMG signals is chosen as the reference region for further calculations to compute a network of the brain regions significantly coherent to this reference region.

In the next step, directional information flow between the coherent cortical sources by the first (cognitive) Bayesian sensor fusion module 108 and muscle modules by the second (spinal) Bayesian sensor fusion module 110 are evaluated with a directional coherence measure (Granger causality), which decomposes signals within cortico-spinal-muscle closed-loops, and may allow disentangling of causality of an impaired muscle activity and muscle modules. Such movement subtask-specific transient cortical sources and networks extracted offline from the EEG and the EMG recordings are targeted online with neurostimulation methods with an optimized multi-electrode configuration.

In an embodiment, brain stimulation electrode montages are optimized for the cortical targets by the aid of computational modelling with the FEM. To this end, tissue types are distinguished in the volume mesh, such as WM, GM, CSF, skull, skin, and lesion. Further, an individual conductivity values are assigned to the volume mesh where a chronic post-disability lesion is assigned. The conductivity of CSF and anisotropic conductivity values for WM and GM are derived from diffusion tensor imaging (DTI) signal. Further, candidate electrodes are represented as a Dirichlet boundary condition and the 3D Laplace equation is solved for the electric field. In an embodiment, the candidate electrode is at least one of static and time-varying. Many candidate electrode montages can be evaluated iteratively to optimize multi-electrode configuration, for example, the mean induced brain electric field (EF) magnitude at all cortical targets. EF is commonly used to predict the magnitude of neuronal 'modulation' in transcranial direct current stimulation (tDCS).

For example, facilitation of corticospinal excitability of only the affected limb in hemiplegia may be intended, which warrants brain stimulation that is customized with the patient-specific MRI based head model. Therefore, using the above mentioned signal processing techniques, the Signal generator 118 determines the specific dysfunctional anatomical locations in the brain specific to the subtask comparing with normative data the information from the first (cognitive) Bayesian sensor fusion module 108 and then the second (spinal) Bayesian sensor fusion module 110 which are stimulated non-invasively using neurostimulation technique via electrical stimulator 106. As mentioned earlier in this paragraph, brain stimulation is achieved by inducing the EF externally in the excitable brain neural tissue such that the intrinsic and extrinsic EF combines to produce normative brain behaviour.

According to another embodiment of the present invention, the system 100 provides visuomotor balance therapy (VBT) to reduce the fall risk in the patients. The visual and sensory signals to the brain, which assist eye-limb co-ordination, are essential to carry out day to day activities. The patients generally lack eye-limb coordination as they are not able to receive and/or coordinate either one or both of visual and sensory signals to the brain.

For example, a patient might see an object clearly but is unable to move his arm to pick up the object as there is no motor signal from the brain to the muscles which means no afferent feedback for sensorimotor integration. The system 100 identifies the defect at the cortical level of the brain and uniquely combines the spinal as well as a supra-spinal feedback, thereby enabling the limb-eye coordination of the patient. The process of integration of the spinal and the supra-spinal feedback with the operant conditioning is explained with the following example in conjunction with FIG. 2.

Figure 2:
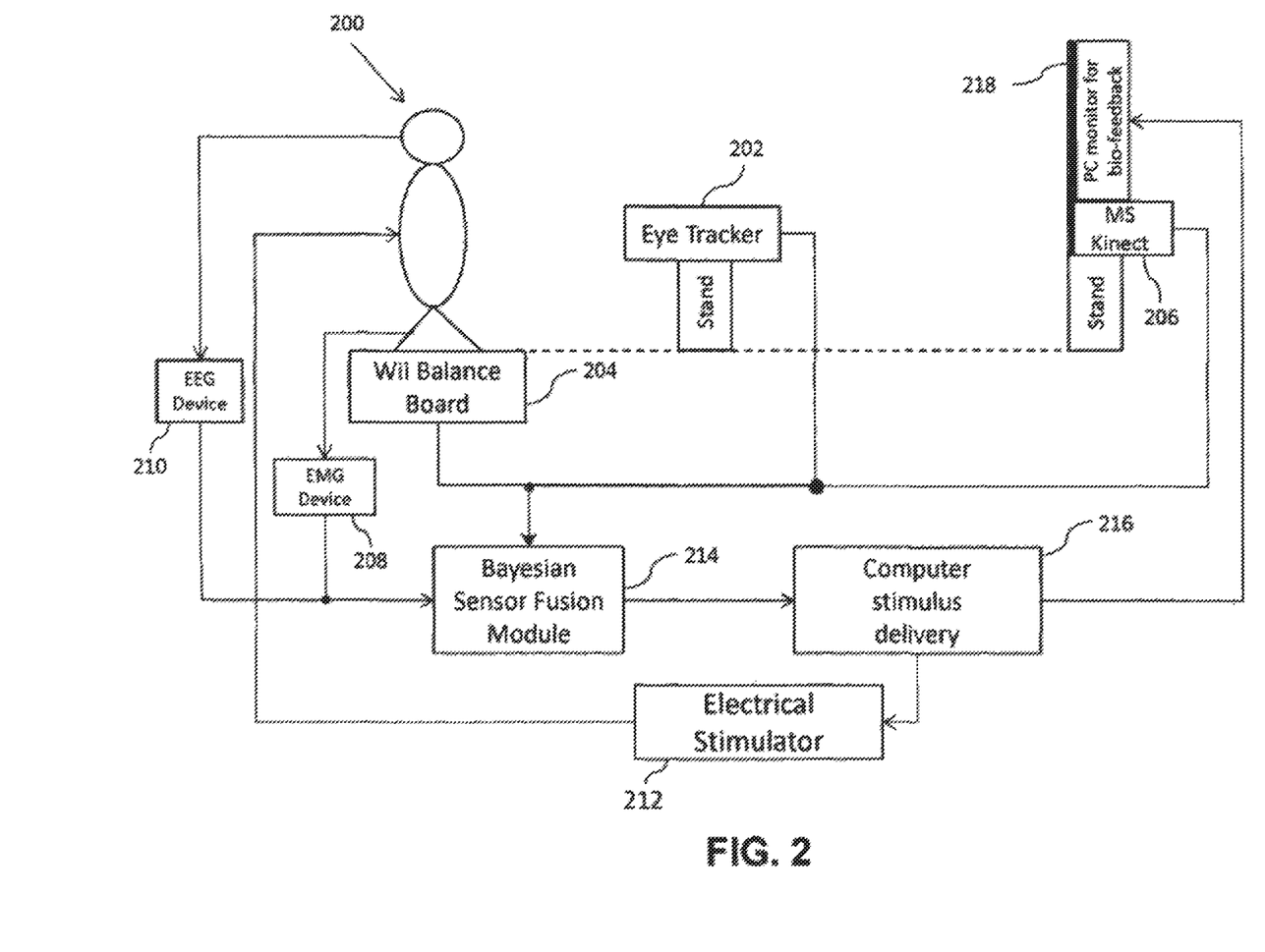
FIG. 2 shows a schematic diagram of the system used to facilitate visuomotor balance rehabilitation therapy, according to another embodiment of the invention.

A system 200 for conducting the VBT using MoBI towards eye gaze based operant conditioning is shown in FIG. 2, in accordance with an exemplary embodiment of the present invention. The system 200 represents a variant of the system 100 previously described. The system 100 and 200, both facilitate the visuomotor rehabilitation therapy of the patient by the means of the eye gaze tracker 102.

The system 200 comprises an eye tracker 202. It should be appreciated that the eye tracker 202 is physically and functionally similar to the eye gaze tracker 102 as described in the previous embodiment. The system 200 is equipped with multiple motion sensors. The motion sensors are configured to detect the change in body position of the patient with respect to the surrounding. In this case, the motion sensors detect the change of at least one of the centre of pressure (CoP) and centre of mass (CoM) of the patient under observation. In an example, the system 200 uses a WII Balance Board 204 (trademark owned by Nintendo, USA) for measuring CoP signals and a MS KINECT 206 (trademark owned by Microsoft, USA) for measuring CoM signals of the patient as shown in FIG. 2. However, it should be appreciated that the use of any other motion sensors such as passive infrared (PIR) sensors, microwave sensors, inertial measurement unit, 3D camera, depth camera, ultrasonic motion, and vibration motion sensors and the like is well within the scope of the present invention.

The system 200 in addition to motion sensors comprises multiple biosensor units 208 and 210, which detect the biological signal of the patient and convert it into electrical signals. In an embodiment of the invention, the system 200 comprises an electromyogram (EMG) device 208 for detecting the electrical potential generated by the muscle cells, an electroencephalogram (EEG) device 210 for detecting the electrical activity of the neurons in the brain and the eye tracker 202 for measuring various eye parameters. However, it should be appreciated that the use of any other biosensors unit such as an electrocardiography (ECG) device, an electrodermography (EDG) device, a diffuse optical imaging system, a magnetic resonance imaging device (MRI) and the like is well within the scope of the present invention. The system 200 also comprises transcutaneous electrical stimulator 212, a Bayesian sensor fusion module 214, a computer stimulus delivery 216, and a PC monitor 218 for displaying visual bio-feedback.

The eye tracker 202 that can be a standalone computer system is connected to the Bayesian sensor fusion module 214. The patient has to sit at the desk at a distance of approximately 50 cm from the eye tracker 202. The monitor 218 is adjusted to align the patient's eyes with its center. The eye tracker detects the patient's eyes. The calibration of the eye tracker 202 is carried out with the patient's eyes. The computer 216 executes a virtual reality based program and displays a visual stimulus on the monitor 218. An eye gaze data synchronized with the visual stimulus is acquired by allowing the patient to follow fixed and moving visual stimuli at various positions on the monitor 218, thereby evaluating post-stroke eye movements of the patient. Therefore, the eye tracker 202 acts as a prognostic tool for post-stroke patients.

A virtual environment comprising a football field with a goal post and a ball at the centre of the field is created during the VBT. The virtual environment is created by a processor present in the computer stimulus delivery 216. The monitor 218 is connected to the computer 216 and is used to display the 3D virtual environment to the patient. In another embodiment of the invention, the virtual environment can be created using a Head Mounted Display (HMD) or a cave automatic virtual environment (CAVE) system. The therapy is designed to be conducted in three phases. In the first phase, the patient is made to stand on the WII balance board 204 with minimum baseline neuromuscular electrical stimulation (NMES) level necessary to generate basic support for upright standing. The first phase is referred as a 'Central Hold Phase'. From the 'Central Hold Phase', the patient moves into a 'Move Phase' (second phase), where the patient steers the virtual object, i.e., the ball as fast as possible towards a randomly presented peripheral target such as a goal post. The 'Move Phase' is followed by a 'Peripheral Hold phase' (third phase) where the patient has to hold the ball in the existing position for one second. Following the 'Peripheral Hold phase' the ball will automatically reset back to the centre of the football field. The patient will try to follow the movement of the ball and will try to recover back to his original upright position when the ball resets back to the centre of the football field.

Generally, the patient will be unable to volitionally recover to his original upright position from the 'Peripheral hold phase' due to lack of limb-eye coordination. The CoM and CoP of the patient shifts to such an extent that the patient losses his balance and is on the verge of tipping off from the WII balance board 204. The ideal CoM and CoP values of a healthy individual are pre-stored in the memory of the Bayesian Sensor Fusion Module 214. The Bayesian Sensor Fusion Module 214 receives CoP and CoM signal values from the WII balance board 204 and the MS KINECT 206, respectively. The Bayesian Sensor Fusion Module 214 compares the CoP and CoM signal values with the ideal values. The computer stimulus delivery 216 then sends an input signal to transcutaneous electrical stimulator 212 based on the deviation of the CoP and CoM signal values from the ideal values. The transcutaneous electrical stimulator 212, upon receiving the input signal provides an electrical stimulation (NMES and SES) to the patient, thereby helping him/her to recover to his original upright position. All devices used in VBT and the signals collected from these devices are cued with visual bio-feedback.

During the course of the VBT, the patient is made to stand on the WII balance board 204. The patient volitionally shifts the posture of his body to steer the ball from one phase to the next, without tipping off from the WII balance board 204, thereby shifting his/her CoP. The CoM is estimated from the 'Skeleton Tracking' data captured by the MS KINECT 206. The CoM is a position in space, where the entire mass of a body is considered to be located at that position. The CoM depends on the posture of the body and the body can maintain static balance as long as the CoM is maintained within the support area, which in this case, is the distance between the feet of the patient. The instantaneous change in the CoP and the CoM values due to postural sway of the body is computed by the Bayesian sensor fusion module 214 and transferred to the computer 216 which in turn is cued with the monitor 218 giving real time visual bio-feedback. An operant conditioning paradigm will incorporate the electrical stimulation via electrical stimulator 212 targeted to aid the patient to improve his standing balance ability.

In one embodiment, the operant conditioning involving the patient's movement with respect to a certain target may be controlled by using visual feedback, physical parameters coordinates such as the CoP and the CoM, and a cursor acceleration using certain dynamics. The cursor acceleration refers to the virtual object acceleration that the patient may be asked to move or control. The dynamics to integrate the operant conditioning with the computer 216 are given as:

$$\begin{bmatrix} \ddot{x} \\ \ddot{y} \end{bmatrix}_{Cur} = \varepsilon_1 \begin{bmatrix} x \\ y \end{bmatrix}_{CoP_1} + \varepsilon_2 \begin{bmatrix} x \\ y \end{bmatrix}_{CoP_2} - \alpha \begin{bmatrix} x \\ y \end{bmatrix}_{Cur} - \beta \begin{bmatrix} \dot{x} \\ \dot{y} \end{bmatrix}_{Cur} + \eta$$

where $\varepsilon_1$, $\varepsilon_2$ parameterizes the effect of recorded $CoP_1$, $CoP_2$ sensor coordinates excursions $$\begin{bmatrix} x \\ y \end{bmatrix}_{CoP_1} \text{ and } \begin{bmatrix} x \\ y \end{bmatrix}_{CoP_2}$$

on the cursor acceleration, $$\begin{bmatrix} \ddot{x} \\ \ddot{y} \end{bmatrix}_{Cur}$$

and $\alpha$ and $\beta$ parameters prevent the cursor from going off-screen, and $\eta \square N(0, \sigma_P)$ represents the process noise with variance $\sigma_P$. The increase in gain $\varepsilon_1$, $\varepsilon_2$ makes the task require a lower sensor excursion range while a decrease in the variance $\sigma_P$ reduces the uncertainty. The difficulty of the task can be increased by decreasing the gain $\varepsilon_1$, $\varepsilon_2$ and increasing the variance $\sigma_P$. Visual deprivation may be effected by introducing an observer noise in the visual feedback by flashing a low contrast dot on the screen with a position drawn from radially isotropic Gaussian distribution centered on the true position of the cursor. The variance representing this Gaussian cloud of points $N(0, \sigma_o)$ will introduce the observer noise. Therefore, the difficulty of the task can be modulated spatiotemporally with parameters $\sigma_p$ and $\sigma_o$ for the affected and unaffected limbs during operant conditioning. For an example, the gain $\varepsilon_1$, $\varepsilon_2$ can be set individually for the affected and unaffected limbs for each peripheral target such that similar reaching errors are presented during the exploratory stage of visuomotor learning, which leads to comparable reward expectations and thereby operant conditioning of the visuomotor learning.

During the course of the VBT, the eye tracker 202 captures the gaze behaviour of the patient such as saccades, blinks, fixation pattern, eye blinks, and smooth pursuit behaviour and transmits the signal to the Bayesian Sensor Fusion Module 214 and then to the Computer stimulus delivery 216. When the muscle cells are neurologically activated by the stimulation given by the transcutaneous electrical stimulator 212, the EMG device 208 detects the electrical potential generated by the stimulated muscle cells. Surface EMG signal is collected from the paretic muscles by the EMG device 208. EEG signal, i.e., the electrical activity of the neurons of the brain is collected by the EEG device 210. The surface EMG signal and EEG signal are superimposed in the Bayesian sensor fusion module 214. The Bayesian sensor fusion module 214 generates an output signal and transmits it to the computer stimulus delivery 216. The CoP value, the CoM value, the gaze behaviour pattern, the skeleton tracking signal, the EMG signal, and the EEG signal are acquired by the Bayesian Sensor Fusion Module 214. The Bayesian Sensor Fusion Module 214 processes these signals, sends relevant stimulus to computer stimulus delivery 216, and provides a real-time visual biofeedback on the monitor 218. Thus, the system 200 combines both the spinal and the supra-spinal feedback for visuomotor balance therapy to reduce fall risk in stroke survivors.

In an embodiment of the operant conditioning based on gaze behaviour and eye blinks may be used to estimate an attentional processing, where the "attentional blink" may be a result of high-level processing, such as decision making and memory encoding, that is dysfunctional in patients with visuomotor disability. In an embodiment, the attentional blink may be due to a low-level visual information processing. A quiet eye (QE) period, defined as an elapsed time between the last visual fixation to the target and the initiation of the motor response, is a characteristic of higher levels of performance. During visuomotor tasks, a prolonged QE period and a greater cortical activation on the right-central region is exhibited by an experts in the tasks in comparison to the non-experts in the task. Further, the experts in the task consistently exhibit fewer fixations of longer duration than non-experts in the task. Therefore, in the operant conditioning paradigm, subthreshold visual stimuli may be presented out of the time-window of the attentional blink, where no learning may occur for stimuli presented during the attentional blink.

According to another embodiment of the invention, the system 100 also provides reinforcement in the form of a stimuli noise to enforce the patient to volitionally take corrective action when an electrical stimulation is provided. For example, during VBT, if sensory deprivation in one of the legs is more as compared to the other, sensory feedback of that leg may be enhanced by introducing the SES in conjunction with an observer noise in the visual feedback. Positive reinforcement by the patient suffering from visuomotor disability, i.e., a visual stimulus with a loud noise is introduced when the patient performs a desired action more accurately; whereas, negative reinforcement, i.e., a visual stimulus with less noise is provided when a desired action is performed incorrectly. The patient tries to overcome the deficit in the observer noise by performing the desired action correctly. Hence, the paretic leg of the patient is pushed to take corrective action by providing the observer noise reinforcement along with electrical stimulation, while the unaffected limb is penalized to balance the two in a bipedal balance task.

The system 100 of the present invention primarily aims to facilitate VBT for patients suffering from visuomotor disability. However, it should be appreciated that the system 100 can also be used to facilitate other forms of rehabilitation therapies.

In another embodiment of the present invention, the system 100 is configured to provide tele-rehabilitation therapy to the patient suffering from stroke. The system 100 is installed at a distant location such as the patient's residence where the patient's progress can be monitored by the caretaker through tele-rehabilitation. A lower-level JavaScript algorithm is developed to connect the HMI of the system 100 directly from within a web-browser of a tablet, smartphone, PC, laptop, and the like, to facilitate tele-rehabilitation. The web-based interface is configured to connect, configure and control a plurality of physical sensors. The operation of the motion sensors and the biosensor units is controlled from a remote location and the feedback signal is collected, viewed and monitored in real time.

The process of implementation of rehabilitation therapy is integrated into the computer within smart eye system 100 in the form of an algorithm. The smart eye system 100 is applied to eye gaze-based operant conditioning.

The present invention has been described herein with reference to a particular embodiment for a particular application. Although selected embodiments have been illustrated and described in detail, it may be understood that various substitutions and alterations are possible. Those with ordinary skill in the art and access to the present teachings may recognize various additional substitutions and alterations are also possible without departing from the spirit and scope of the present invention, and as defined by the following claims.

What is claimed is:

1. A method to facilitate diagnosis and treatment, using operant conditioning in visuomotor rehabilitation therapy, of a subject having a visuomotor dysfunction, said subject being in loop with an apparatus (100), said method comprising the following steps:

detecting movements of the eye of the subject while performing a visuomotor task and converting the eye movements into eye gaze data (A), during which visuomotor task, the patient's brain provides signals to the spinal system of the subject to generate voluntary torque in the neuromuscular system (114) of the subject for performing the task; and capturing EEG signals from the brain of the subject during the performance of said task and generating EEG data (D);

capturing volitional EMG signals from the muscle stimulated by the spinal system of the subject during said task and generating EMG data (B);

capturing center of pressure (CoP) and center of mass (CoM) signals (C) of the subject while performing the task with the help of physical sensors (120);

transmitting the eye gaze data (A), the EEG data (D), the EMG data (B), and the CoP and CoM signals (C) to a computer comprising: a first Bayesian sensor fusion module (108), a second Bayesian sensor fusion module (110), and a signal generator (118);

processing the eye gaze data (A) and EEG data (D) in the first Bayesian sensor fusion module to generate a first output signal (OS1);

storing a normative EMG signal for performing the task by a healthy age-matched individual in the second Bayesian sensor fusion module (110);

processing the EMG data (B) and the CoP and CoM signals (C), and the first output signal (OS1) as a component with respect to the stored normative EMG signal in the second Bayesian sensor fusion module (110) to generate a second output signal (OS2);

feeding the first output signal (OS1) and the second output signal (OS2) to the signal generator (118);

generating, by the signal generator (118), a visual feedback stimulus (H) to be supplied to the subject to be received by the brain of the subject;

generating, by the signal generator (118), brain template signals, muscle template signals, and sensory activation template signals;

transferring the generated brain template, muscle template, and sensory activation template signals to an electrical stimulator (106);

generating, in the electrical stimulator (106), brain stimulation signals (E) based on the brain template signals, therapeutic motor stimulation signals (J) based on the muscle template signals, and sensory stimulation signals (G) based on the sensory activation template signals;

providing the therapeutic motor stimulation signals (J) to the muscles of the subject;

providing the brain stimulation signals (E) to the brain of the subject;

providing the sensory stimulation signals (G) to the spinal system of the subject to generate evoked torque in the neuromuscular system (114) of the subject;

capturing, in a normal kinematics module (116), the superimposed torque which is combination of the evoked torque and the voluntary torque;

processing, by the normal kinematics module (116), the superimposed torque, generated by the spinal system of the subject to generate a near normal afferent feedback signal (F);

feeding the near normal afferent feedback signal (F) and the sensory stimulation signal (G) to a sensorimotor integration system (112) for generating a sensory feedback (SF) to the brain of the subject to generate a motor signal in the brain which is received by the spinal system of the subject;

receiving said visual feedback stimulus (H) and the sensory feedback signal (SF) by the brain of the subject and generating a motor control signal;

receiving the motor control signal by the spinal system of the subject to allow the subject to enhance muscle activity, and thereby improving the action of the subject while performing the task; and continuing the therapy with the subject in the loop until the subject performs the task accurately/correctly.

2. The method as claimed in claim 1, wherein the method includes delivering a reward to the subject as loud noise in the form of positive reinforcement or by various means including modulating the scores, varying the difficulty, and/ or providing pleasant sensory events to the subject, when the subject performs the task accurately/correctly.

3. A method of performing visuomotor balance therapy (VBT) on a subject having a visuomotor dysfunction to improve the subject's standing balance ability, said method comprising the following steps:

making a subject to stand on a balance board (204) having physical/motion sensors (208, 210);

capturing, by an eye tracker (202) eye gaze behaviour of the eyes of the subject while performing the balance therapy, and generating eye gaze behaviour pattern signals;

detecting, by an EMG device (208) electrical activity of the muscles, and generating EMG signal;

collecting, by an EEG device (210) electrical activity of the neurons of the brain of the subject, and generating EEG signal;

detecting the center of pressure (CoP) and the center of mass (CoM) of the subject upon postural shift of the body of the subject while standing on the board (204) by the board (204) and a camera (206);

generating, by the balance board (204) and the camera (206), CoP and CoM signal values;

receiving, by the Bayesian sensor fusion module (214), detected CoM and CoP values of the subject, EEG signal, EMG signal, and eye gaze pattern signals from the eye tracker (202), the balance board (204), the camera (206), the EMG device (208), the EEG device (210);

processing, by the Bayesian sensor fusion module (214) the received CoP and CoM values, the eye gaze behaviour pattern signal, the EEG signal, the EMG signal and generating a stimulus signal;

receiving, by a computer stimulus delivery device (216), the stimulus signal form the Bayesian sensor fusion module (214), and generating an input signal;

receiving, by a PC monitor (218), the input signal from the computer stimulus delivery (216), and proving a visual feedback to the subject in a virtual environment steering a ball from one phase to the next in accordance with the postural shift of the subject; and receiving, by an electrical stimulator (212), the input signal from the computer stimulus delivery (216), and providing electrical stimulations to the subject, thereby helping him to recover to his original upright position and improving his standing balance ability.

4. Apparatus (100) for carrying out the method of claim 1, said apparatus (100) comprising:

an eye tracker (102) configured to detect the movements of the eye of the subject while performing the task, and further configured to convert the eye movements into eye gaze data (A), during which visuomotor task, the patient's brain provides signals to the spinal system of the subject to generate voluntary torque in the neuromuscular system (114) of the subject for performing the task;

an EEG device (104b) configured to capture EEG signals from the brain of the subject during the task, and further configured to generate EEG data (D);

an EMG device (104a) configured to capture EMG signals from the muscle stimulated by the spinal system of the subject during the task, and further configured to generate EMG data (B);

physical sensors (120) configured to capture center of pressure (CoP) and center of mass (CoM) of the subject while performing the task, and further configured to generate CoP and CoM signals (C);

a computer system comprising:

a first Bayesian sensor fusion module (108) configured to receive and process eye gaze data (A) and EEG data (D) to generate a first output (OS1);

a second Bayesian sensor fusion module (110) configured to store a normative EMG signal of a healthy age-matched individual, said second Bayesian sensor fusion module (110) further configured to receive and process the EMG data (B) and the CoP and CoM signals (C), and the first output (OS1) as a component with respect to the stored normative EMG signal to generate a second output (OS2); and a signal generator (118) configured to receive the first output (OS1) and the second output (OS2), and further configured to generate a visual feedback stimulus (H) to be supplied to the subject, and generate brain template signals, muscle template signals, and sensory activation template signals, an electrical stimulator (106) configured to receive the generated brain template, muscle template, and sensory activation template signals, and further configured to generate brain stimulation signals (E), motor stimulation signals (J), and sensory stimulation signals (G), and further configured to provide the motor stimulation signals (J) to the muscles of the subject, brain stimulation signals (E) to the brain of the subject, and sensory stimulation signal (G) to the spinal system of the subject to generate evoked torque in a neuromuscular system (114) of the subject;

a normal kinematics module (116) configured to receive a superimposed torque which is combination of the evoked torque and the voluntary torque from the neuromuscular system (114) of the subject, and further configured to process the superimposed torque, and generate a near normal afferent feedback signal (F);

a sensorimotor integration system (112) configured to receive the near normal afferent feedback signal (F) from the normal kinematics module (116) and the sensory stimulation signal (G) from the electrical stimulator (106), and further configured to integrate the near normal afferent feedback signal (F) and the sensory stimulation signal (G) to generate a sensory feedback signal (SF) to be supplied to the brain of the subject; and said sensory feedback signal (SF) generated by sensorimotor integration system (112) and said visual feedback stimulus (H) generated by the signal generator (118) when supplied to the brain of the subject, allow the brain to generate motor control signal to be supplied to the spinal system of the subject to enhance the muscle activity to improve action of the subject while performing the task.

5. The apparatus (100) as claimed in claim 4, wherein the eye tracker module (102) comprises a desktop remote device with an inbuilt camera, an infrared emitter, frame grabbers, an optical filter, and a controller with an algorithm for processing an image obtained through a video oculography.

6. The apparatus (100) as claimed in claim 4, wherein said computer system includes at least a processor, and a memory with a computer-readable medium having a computer code stored therein for execution by the processor to allow the computer system to carry out the described diagnosis and treatment upon execution of the code.

7. The apparatus (100) as claimed in claim 4, wherein said computer system includes an algorithm that facilitates apparatus (100) to connect with a web-browser of a tablet, a smartphone, a PC, a laptop, and the like, to facilitate tele-rehabilitation.

* * * * *